(12) United States Patent
Millot

(10) Patent No.: US 6,391,015 B1
(45) Date of Patent: May 21, 2002

(54) METHOD FOR MEASURING THE CUTANEOUS ELECTRICAL RESISTANCE OF A PATIENT SUBJECTED TO TRANSDERMAL ADMINISTRATION OF MEDICINE

(75) Inventor: Philippe Millot, Orgeux (FR)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/312,498

(22) Filed: May 17, 1999

(51) Int. Cl.$^7$ ............................................. A61M 31/00
(52) U.S. Cl. .................................................. 604/503
(58) Field of Search ..................... 604/503, 500–501, 604/20, 48; 607/149, 153, 62, 59

(56) References Cited

U.S. PATENT DOCUMENTS

| 3,866,600 A | 2/1975 | Rey ........................ 128/2.1 R |
| 4,141,359 A | * 2/1979 | Jacobsen et al. ......... 128/172.1 |
| 5,426,387 A | 6/1995 | Teillaud et al. ............. 377/107 |
| 5,499,967 A | 3/1996 | Teillaud et al. ................ 604/20 |
| 6,141,582 A | * 10/2000 | Mori et al. ..................... 604/20 |

FOREIGN PATENT DOCUMENTS

| DE | 40 28 125 | 7/1991 |
| EP | 0 558 409 | 9/1993 |
| WO | WO89/06555 | 7/1989 |
| WO | WO95/06497 | 3/1995 |

* cited by examiner

*Primary Examiner*—Anhtuan T. Nguyen
*Assistant Examiner*—Ann Y Lam
(74) *Attorney, Agent, or Firm*—Factor & Partners

(57) ABSTRACT

In accordance with the invention, an ionophoresis current (I) assisting administration is temporarily adjusted to a predetermined value ($I_m$) corresponding to a point on a rectilinear portion ($O_A$) adjoining the origin of the current/voltage characteristics of the skin of the patient, the voltage ($V_{skin}$) then present between the two electrodes applying the ionophoresis current to the skin of the patient is measured and the measured cutaneous resistance ($R_{cut}$) is obtained from the measured voltage ($V_{skin}$) and the predetermined value ($I_m$) of the ionophoresis current.

31 Claims, 1 Drawing Sheet

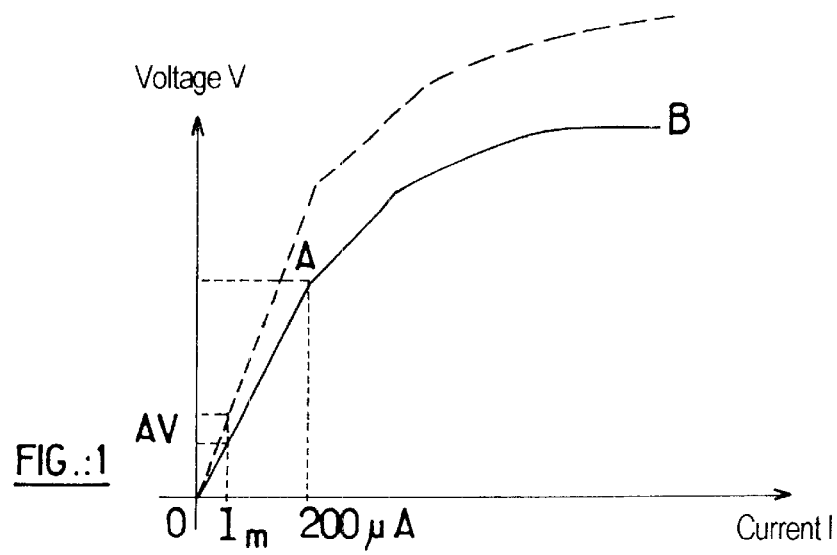
FIG.:1
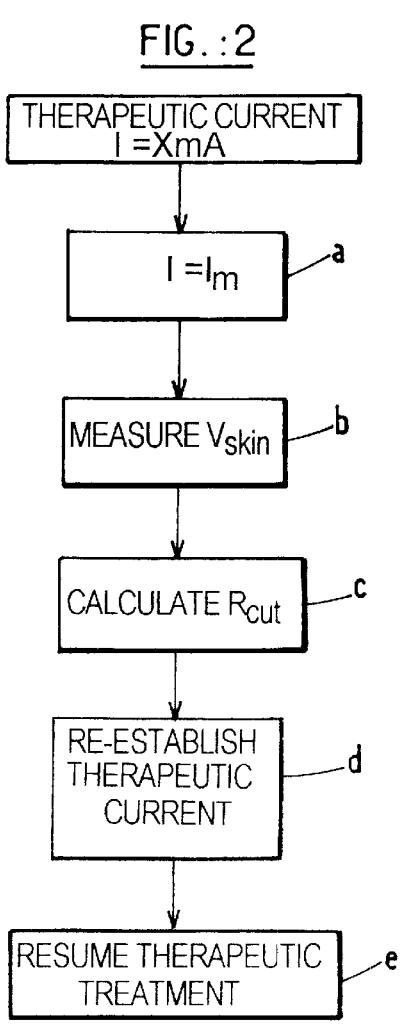
FIG.:2
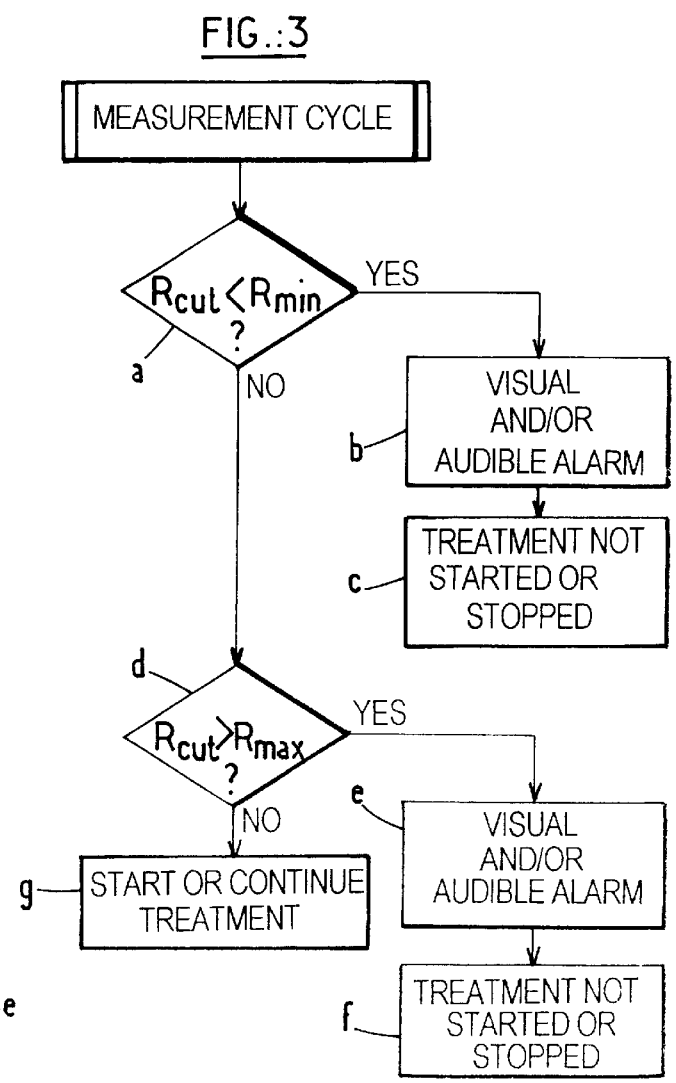
FIG.:3

METHOD FOR MEASURING THE CUTANEOUS ELECTRICAL RESISTANCE OF A PATIENT SUBJECTED TO TRANSDERMAL ADMINISTRATION OF MEDICINE

The present invention concerns a method of measuring the cutaneous electrical resistance of a patient and, more particularly, a method of this kind used on a patient undergoing transdermal administration of medication assisted by an ionophoresis current.

BACKGROUND OF THE INVENTION

Many devices have been designed for ionophoretic administration of medication. That described in French patent application n° 96 04735 filed Apr. 16, 1996 by the Applicant may be cited as one example. Administration in this way implies the use of an active principle taking an ionic form susceptible, under the action of an electric field, to pass through the skin of the patient. The field is established between two adjacent electrodes applied to he skin of the patient. The administration of the medication develops conventionally in accordance with a time programme including periods of administration optionally separated by periods of non-administration during which the ionophoresis, or "therapeutic", current is cut off. During periods of administration the current may be set at predetermined values, for example 500 µA, 750 µA, that can differ from one period to another. The total duration of an administration programme is routinely measured in hours, even in days.

The application of an electric current to a surface element of the skin of a patient for periods of time this long can modify the characteristics of the skin, and even cause lesions, from slight superficial oedema to deep burns, accidents that obviously have to be prevented by constant monitoring of the status of the skin surface element subjected to the ionophoresis current.

This monitoring is routinely effected by monitoring the electrical resistance of this surface element of the skin of the patient, as a modification of the structure of the skin, due to the imminent appearance of a lesion, is manifested in a variation in said cutaneous electrical resistance.

Conventionally, to measure this electrical resistance the electrical voltage between the electrodes applied to the skin of the patient is noted at the time of the measurement. These electrodes are part of an ionophoresis assisted transdermal administration device that includes means for adjusting the ionophoresis current.

Knowing the voltage between the electrodes and the current, a measured value for the cutaneous resistance of the patient within the current tube limited by the two surface elements of his skin covered by said electrodes can be deduced, simply by application of Ohm's law. In the following, said electrical resistance is called "cutaneous" resistance of the patient.

Incidentally, note that this voltage also enables diagnosis of malfunctions of the device, for example short-circuiting of the skin by sweat on the surface of the skin, insufficient hydration of a reservoir of active principle joined to an electrode, etc, etc, . . .

The voltage measurement referred to above does not enable reliable conclusions to be drawn from the observed variations in the measured values, however, because the current/voltage characteristic of the skin is not linear, as can be seen from the graph of this characteristic represented in FIG. 1 of the accompanying drawing.

This graph, established with electrodes having a surface of 4 cm$^2$ and from measurements taken without any significant modification of the structure of the skin appearing, shows that, depending on the value of the ionophoresis current I at the times the voltage is measured, the cutaneous resistance as measured using said law can take different values even if the structure of the skin has not deteriorated at all from one measurement to the other. It therefore appears that the voltage measurements mentioned hereinabove cannot provide a reliable diagnosis of the imminent appearance of a lesion in the skin surface element subjected to the ionophoresis current.

An aim of the present invention is to provide a method of measuring the cutaneous electrical resistance of a patient undergoing ionophoresis assisted transdermal administration of medication that can reliably diagnose the imminent appearance of a lesion of this kind.

Another aim of the present invention is to provide a method of the above kind that can also diagnose the occurrence or the existence of malfunctions of the device used to perform the ionophoresis assisted transdermal administration of the medication.

SUMMARY OF THE INVENTION

These aims of the invention, and others that will emerge from a reading of the following description, are achieved with a method of the type described in the preamble to this description, this method being noteworthy in that the ionophoresis current is temporarily adjusted to a predetermined value corresponding to a point on a rectilinear portion adjoining the origin of the current/voltage characteristics of the skin of the patient, the voltage then present between the two electrodes supplying the ionophoresis current to the skin of the patient is measured and the measured cutaneous resistance is obtained from the measured voltage and the predetermined value of the ionophoresis current.

As will be shown in more detail hereinafter, by setting the value of the current in this way at the time the voltage is measured, the problem of the non-linearity of the current/voltage characteristic of the skin likely to interfere with the diagnosis of the imminent appearance of a lesion on the skin of the patient is avoided.

According to another feature of the method of the invention, said predetermined value of the ionophoresis current is a value corresponding to a substantially zero flux of the medication through the skin of the patient.

BRIEF DESCRIPTION OF THE DRAWING

Other features and advantages of the invention will emerge from a reading of the following description and from an examination of the accompanying drawing, in which:

FIG. 1 is a graph of the current/voltage characteristic of the skin, as discussed in the preamble to the present description, FIG. 2 is a flowchart showing one embodiment of the measuring method of the invention, and FIG. 3 is a flowchart showing the exploitation of the measurements obtained by the method of the invention.

DESCRIPTION OF A PREFERRED EMBODIMENT

FIG. 1 of the accompanying drawing shows that the current/voltage characteristic of the skin of a human being has a rectilinear part 0A starting from the origin 0 and a curvilinear part AB, the threshold A between these parts typically corresponding to a current of 200 µA, measured between two adjacent electrodes each of a surface area of 4 cm², which corresponds to a current density of 50 µA/cm².

In accordance with one feature of the present invention, this observation is exploited to render the voltage measurement intended to yield the cutaneous resistance of the skin independent of the non-linearity of the part AB. To this end, when the voltage is measured, the ionophoresis current is adjusted to a value $I_m$ in a range of variation corresponding to the rectilinear part 0A, i.e. in the range 0–200 µA. This current may be set to 50 µA, for example, which corresponds to a current density of 12.5 µA/cm², a low level of current density that corresponds to a substantially zero flux of the active principle through the skin, which is not likely to interfere with the resistance measurement to be carried out.

Accordingly, assuming that, at the time of the measurement, the current/voltage characteristic of the skin is no longer that shown in full line but that shown in dashed line, because the structure of the skin has deteriorated due to the passage of the ionophoresis, or "therapeutic", current, the difference ΔV between the measured voltages on these two curves is exactly and exclusively representative of the variation of the slope of the straight line part of the characteristic, this slope corresponding to the required resistance of the skin in the current range 0–200 µA, or 0–50 µA/cm². This would not be the case in the non-linear part of the characteristic.

Furthermore, the slope variation is measured with reference to the slope of the segment 0A of the characteristic 0AB corresponding to sound skin. Accordingly the measured voltage variation is perfectly representative of the deterioration in the structure of the skin resulting from the application of an ionophoresis current to initially sound skin. In this way it is possible to detect the imminence of a degraded state of the skin, oedema, burn or otherwise, that is to be prevented, and to stop the transdermal treatment before this state supervenes. This prevents both unacceptable deterioration of the skin of the patient and continuance of the treatment on degraded skin, which would otherwise prevent correct execution of the treatment.

One embodiment of the measuring method of the invention will now be described in more detail with reference to FIG. 2 of the accompanying drawing. The method can be executed before a treatment is started, to verify that the state of the skin of the patient and that of the transdermal administration device used are suitable for such administration, as explained below with reference to FIG. 3. The method can also be executed during the treatment, for example at regular intervals, in order to monitor the same states and to decide whether to continue the treatment or to stop it, depending on the states diagnosed.

In the case of execution during treatment the electronics of the administration device, which is of the type described in the previously mentioned French patent application, for example, are programmed to reduce the ionophoresis current X mA that it delivers (for example 500 µA) to the level $I_m$ previously mentioned, located in the rectilinear part 0A of the characteristic from FIG. 1, this level being sufficiently low to create no significant ionophoresis flux that could interfere with the measurement to be made. As mentioned above, this current level, or "measuring current", $I_m$ can thus be set at 50 µA (or 12.5 µA/cm²), for example (step a, FIG. 2).

After establishing this current and maintaining it for a certain time, for example three seconds, to enable the value that is to be measured to stabilise and possibly to enable the skin to become depolarized, the device measures the voltage $V_{skin}$ between the electrodes applied to the skin of the patient (step b) and calculates the cutaneous resistance $R_{cut}$ (step c) using Ohm's law.

$$R_{cut} = \frac{V_{skin}}{I_m}$$

When the measurement has been made, the ionophoresis or "therapeutic" current between the electrodes is progressively returned to the previous level X mA. To achieve this, it is possible to establish, for example, X/4 mA, X/2 mA, 3X/4 mA, each time for one second, before returning to X mA (step d). Naturally other schemes for increasing the current before resuming the therapeutic treatment could be used instead, provided that they prevent sudden return to the X mA level being uncomfortable for the patient.

The measurement method described hereinabove can be used either during application of the therapeutic current X mA or during periods in which there is no such current, so that the state of the device and of the skin can be monitored continuously. Accordingly, sweating of the skin can be detected as well as the short-circuiting of the electrodes that it may cause.

It will be noticed that the measurements made when the therapeutical current is null exhibit a good precision, in particular when the measurement is made at the end of such a period. As a matter of fact, the measurement is not then disturbed by the polarization of the skin, a depolarizing time having been spent before the measurement.

Execution of the measuring method of the invention can be triggered and controlled automatically by the electronics of the transdermal application device employed. The measurement can be triggered at predetermined regular time intervals during treatment, for example. The duration of the time period can be chosen in the range 20 seconds to 15 minutes. A period of three minutes is preferably chosen.

How the electronics of the administration device exploit the cutaneous resistance measurements obtained, both before starting a treatment and during the latter, will now be explained with reference to the flowchart in FIG. 3.

The electronics are programmed to compare the measured value $R_{cut}$ of the cutaneous resistance to a threshold value $R_{min}$ (step e). This threshold can be set to between 100 and 1000 ohms, typically to 500 ohms, when electrodes of 4 cm² area are used.

If $R_{cut}$ is less than $R_{min}$ and $R_{cut}$ is measured before the treatment is started, a visual and/or audible alarm is given (step b) to advise the patient of the probable existence of a short-circuit between the electrodes of the device, preventing correct administration of the treatment. Starting of the treatment is prohibited (step c). If this situation is detected during treatment, it is stopped.

If, on the other hand, $R_{cut}$ is greater than $R_{min}$, the electronics of the device then compare $R_{cut}$ to another threshold $R_{max}$ (step d) that can be set to between 50 and 300 kohms, typically 100 kohms.

If $R_{cut}$ is greater than $R_{max}$ this situation is reported to the patient by an audible and/or visual alarm (step e) and starting or continuance of the treatment is prohibited (step f). This situation can be the result of deterioration of the skin structure likely to lead imminently to a lesion of the type mentioned above. It may also be the result of a fault in the transdermal administration device itself.

The reservoir(s) of active principle joined to the electrodes are routinely charged, or "hydrated", before the treatment with an ionic solution of the active principle to be administered. If this hydration is incomplete the active principle cannot be administered satisfactorily and it is then necessary to prohibit the starting or the continuance of the treatment and to trip the available alarms to advise the patient of the necessity to check the hydration status of the reservoir(s).

This check is also needed to continue the treatment in accordance with the preprogrammed conditions. If the measurement yields R=100 kohms, for example, when the programmed therapeutic current is I=1 mA, the voltage to be applied between the electrodes would be 100 volts, a value much too high to be applied without burning the patient.

If, after steps c), d), it appears that $R_{min} < R_{cut} < R_{max}$, the treatment can start or continue (step g).

Of course, the thresholds $R_{min}$ and $R_{max}$ can be set to different levels for measurements before and during treatment, respectively, so that the sensitivity for detecting faults and the sensitivity for detecting lesions are different.

Thus during treatment it is possible to detect the imminent appearance of a lesion (oedema or burn, for example) and to halt the treatment before the lesion occurs, which assures the safety of the patient, in accordance with the essential aim of the present invention.

This safety feature is particularly necessary when administering highly active medication such as some narcotic analgesics, for example phentanyl and its derivatives, that can be dangerous if administered in doses departing from those precisely determined by pharmacological studies. Undetected deterioration of the skin of the patient could lead to dangerous administration of the medication.

Of course, the invention is not limited to the administration of these narcotic analgesics and to the contrary extends to others: morphine, buprenorphine and derivatives, and even to any active principle suitable for ionophoresis assisted transdermal administration.

What is claimed is:

1. A method for measuring the cutaneous electrical resistance of a patient undergoing transdermal administration of medication assisted by an iontophoresis current, wherein the current is applied across a surface of a patient using an iontophoretic device, the iontophoretic device comprising a reservoir having a medicament, a first electrode and a second electrode, the method comprising the steps of:

temporarily adjusting the current from a treatment current density to a predetermined current density, wherein the predetermined current density is within a range of values for which the current density and the voltage have a direct relationship;

measuring the voltage drop across the surface of a patient between the first electrode and the second electrode; and calculating the resistance of the surface of a patient at a region between the first and second electrodes from the measured voltage value and the predetermined current density.

2. The method according to claim 1, wherein the predetermined current density corresponds to a substantially zero current flux of the medicament to be delivered iontophoretically.

3. The method according to claim 1 further including the step of returning the predetermined current density back to substantially the same value as the treatment current density.

4. The method according to claim 3, wherein the steps are repeated at least once during the administration of medicament to a patient.

5. The method according to claim 3, wherein the step of returning the current density comprises the steps of:

changing the predetermined current density to at least one intermediate current density;

maintaining that intermediate current density for a period of time; and changing the intermediate current density to the treatment current density.

6. The method according to claim 1, wherein the method further comprises the steps of:

comparing the calculated resistance with a predetermined minimum resistance;

determining if the calculated resistance is less than the minimum resistance; and changing the treatment current density to zero if the calculated resistance is less than the minimum resistance.

7. The method according to claim 6, wherein the method further comprises the step of activating at least one of an audible and a visual alarm if the calculated resistance is less than the minimum resistance.

8. The method according to claim 6, wherein the method comprises the step of determining the minimum resistance so that a short-circuit of the surface of a patient may be detected.

9. The method according to claim 1, wherein the method further comprises the steps of:

comparing the calculated resistance with a predetermined maximum resistance;

determining if the calculated resistance is greater than the maximum resistance; and changing the treatment current density to zero if the calculated resistance is greater than the maximum resistance.

10. The method according to claim 9, wherein the method further comprises the step of activating at least one of an audible and a visual alarm if the calculated resistance is greater than the maximum resistance.

11. The method according to claim 9, wherein the method comprises the step of determining the maximum resistance so that at least one of a lesion on the surface of a patient, the imminent appearance of a lesion on the surface of a patient, and insufficient hydration of the medicament may be detected.

12. The method of claim 1, wherein there is a predetermined minimum resistance and a predetermined maximum resistance associated with the surface of a patient, the method further comprising the steps of:

determining whether the calculated resistance is between the predetermined values of the minimum resistance and the maximum resistance; and administering the treatment current density if the calculated resistance is between the predetermined values of the minimum resistance and the maximum resistance.

13. The method according to claim 1, wherein the measuring of the cutaneous electrical resistance is performed prior to administering a medicament to a patient.

14. The method according to claim 1, wherein the measuring of the cutaneous electrical resistance is performed after administering medicament to a patient.

15. The method according to claim 1, wherein the predetermined current density is in the range of about 0–50 $\mu$/cm2.

16. The method according to claim 15, wherein the predetermined current density is about 12.5 $\mu$A/cm2.

17. A method for measuring the cutaneous electrical resistance of a patient undergoing transdermal administration of medication assisted by an iontophoresis current, wherein the current is applied across a surface of a patient using an iontophoretic device, the iontophoretic device comprising a reservoir having a medicament, a first electrode and a second electrode, the method comprising the steps of:

temporarily adjusting the current from a treatment current density to a predetermined current density, wherein the predetermined current density corresponds to a substantially zero current flux of the medicament to be delivered iontophoretically;

measuring the voltage drop across the surface of a patient between the first electrode and the second electrode; and calculating the resistance of the surface of a patient at a region between the first and second electrodes from the measured voltage value and the predetermined current density.

18. The method according to claim 17 further including the step of returning the predetermined current density back to substantially the same value as the treatment current density.

19. The method according to claim 18, wherein the steps are repeated at least once during the administration of medicament to a patient.

20. The method according to claim 18, wherein the step of returning the current density comprises the steps of:

changing the predetermined current density to at least one intermediate current density;

maintaining that intermediate current density for a period of time; and changing the intermediate current density to the treatment current density.

21. The method according to claim 17, wherein the method further comprises the steps of:

comparing the calculated resistance with a predetermined minimum resistance;

determining if the calculated resistance is less than the minimum resistance; and changing the treatment current density to zero if the calculated resistance is less than the minimum resistance.

22. The method according to claim 21, wherein the method further comprises the step of activating at least one of an audible and a visual alarm if the calculated resistance is less than the minimum resistance.

23. The method according to claim 21, wherein the method comprises the step of determining the minimum resistance so that a short-circuit of the surface of a patient may be detected.

24. The method according to claim 17, wherein the method further comprises the steps of:

comparing the calculated resistance with a predetermined maximum resistance;

determining if the calculated resistance is greater than the maximum resistance; and changing the treatment current density to zero if the calculated resistance is greater than the maximum resistance.

25. The method according to claim 21, wherein the method further comprises the step of activating at least one of an audible and a visual alarm if the calculated resistance is greater than the maximum resistance.

26. The method according to claim 24, wherein the method comprises the step of determining the maximum resistance so that at least one of a lesion on the surface of a patient, the imminent appearance of a lesion on the surface of a patient, and insufficient hydration of the medicament may be detected.

27. The method of claim 17, wherein there is a predetermined minimum resistance and a predetermined maximum resistance associated with the surface of a patient, the method further comprising the steps of:

determining whether the calculated resistance is between the predetermined values of the minimum resistance and the maximum resistance; and administering the treatment current density if the calculated resistance is between the predetermined values of the minimum resistance and the maximum resistance.

28. The method according to claim 17, wherein the measuring of the cutaneous electrical resistance is performed prior to administering a medicament to a patient.

29. The method according to claim 17, wherein the measuring of the cutaneous electrical resistance is performed after administering medicament to a patient.

30. The method according to claim 17, wherein the predetermined current density is in the range of about 0–50 $\mu A/cm2$.

31. The method according to claim 30, wherein the predetermined current density is about 12.5 $\mu A/cm2$.

* * * * *